United States Patent
Saari et al.

(10) Patent No.: US 10,551,286 B2
(45) Date of Patent: Feb. 4, 2020

(54) TESTING SYSTEM AND METHOD FOR APPLYING LOADS TO A TEST SPECIMEN

(71) Applicant: MTS Systems Corporation, Eden Prairie, MN (US)

(72) Inventors: Byron John Saari, Minneapolis, MN (US); Robert Brian Kerr, Apple Valley, MN (US)

(73) Assignee: MTS SYSTEMS CORPORATION, Eden Prairie, MN (US)

(*) Notice: Subject to any disclaimer, the term of this patent is extended or adjusted under 35 U.S.C. 154(b) by 0 days.

(21) Appl. No.: 14/991,724

(22) Filed: Jan. 8, 2016

(65) Prior Publication Data

US 2016/0202160 A1 Jul. 14, 2016

Related U.S. Application Data

(60) Provisional application No. 62/101,367, filed on Jan. 8, 2015.

(51) Int. Cl.
*G01N 3/02* (2006.01)
*G01N 3/32* (2006.01)

(52) U.S. Cl.
CPC .................. *G01N 3/02* (2013.01)

(58) Field of Classification Search
CPC .. G01N 3/02; G01N 3/08; G01N 3/22; G01N 3/04; G01N 2203/0405; G01N 2203/0003; G01N 2203/0226; G01N 220/005; G01N 2203/0222; G01N 3/38; G01N 2203/0007; G01N 2203/0037; G01N 2203/0208; G01N 2203/0017; G01N 2203/021; G01N 3/62;
(Continued)

(56) References Cited

U.S. PATENT DOCUMENTS

| 4,748,854 A * | 6/1988 | Rao ........................ G01N 3/32 73/799 |
| 5,425,276 A * | 6/1995 | Gram ...................... G01N 3/32 73/781 |

(Continued)

FOREIGN PATENT DOCUMENTS

| JP | 2000314730 A | 11/2000 |
| WO | 0194912 A2 | 12/2001 |

(Continued)

OTHER PUBLICATIONS

International Search Report and Written Opinion for corresponding International application No. PCT/US2016/012722, dated Apr. 13, 2016.

*Primary Examiner* — Brandi N Hopkins
(74) *Attorney, Agent, or Firm* — Steven M. Koehler (57) ABSTRACT

An aspect of the invention is a testing system for applying loads to a test specimen. The testing system includes the actuator and the first support portion supporting the actuator. The actuator is configured to support a first end of the test specimen, while a second support portion configured to support a second end of the test specimen. In various embodiments, combination of sensors that can include displacement sensor and/or accelerometer(s) provide associated output signals that are received by a displacement compensator that is configured to provide a displacement output signal indicative of differential displacement between first end and the second end of the test specimen.

27 Claims, 4 Drawing Sheets

(58) Field of Classification Search
CPC ......... G05B 15/02; G01P 21/02; G01B 3/008;
G01B 21/045; G01B 7/34; G01D 18/00;
G01D 5/2417; G01L 25/00; G01Q 40/00
USPC ................ 73/788, 818, 826, 847, 799, 843,
73/856–857
See application file for complete search history.

(56) References Cited

U.S. PATENT DOCUMENTS

| | | | |
|---|---|---|---|
| 5,581,040 A * | 12/1996 | Lin .......................... | G01N 3/04 |
| | | | 73/833 |
| 7,331,209 B2 | 2/2008 | Saari et al. | |
| 9,689,784 B2 * | 6/2017 | Cerutti ..................... | G01N 3/38 |
| 2002/0017146 A1 * | 2/2002 | Oliver ...................... | G01N 3/08 |
| | | | 73/856 |
| 2005/0267695 A1 | 12/2005 | Oliver | |
| 2008/0011094 A1 | 1/2008 | Saari et al. | |
| 2008/0173104 A1 | 7/2008 | German | |
| 2009/0210158 A1 | 8/2009 | Oliver | |
| 2013/0305840 A1 | 11/2013 | Saari et al. | |
| 2014/0345358 A1 | 11/2014 | White | |
| 2016/0245733 A1 * | 8/2016 | Cerutti ..................... | G01N 3/38 |

FOREIGN PATENT DOCUMENTS

| | | |
|---|---|---|
| WO | 2008005328 A2 | 1/2008 |
| WO | 2014189678 A2 | 11/2014 |

\* cited by examiner

TESTING SYSTEM AND METHOD FOR APPLYING LOADS TO A TEST SPECIMEN

BACKGROUND

The discussion below is merely provided for general background information and is not intended to be used as an aid in determining the scope of the claimed subject matter.

Figure 1:
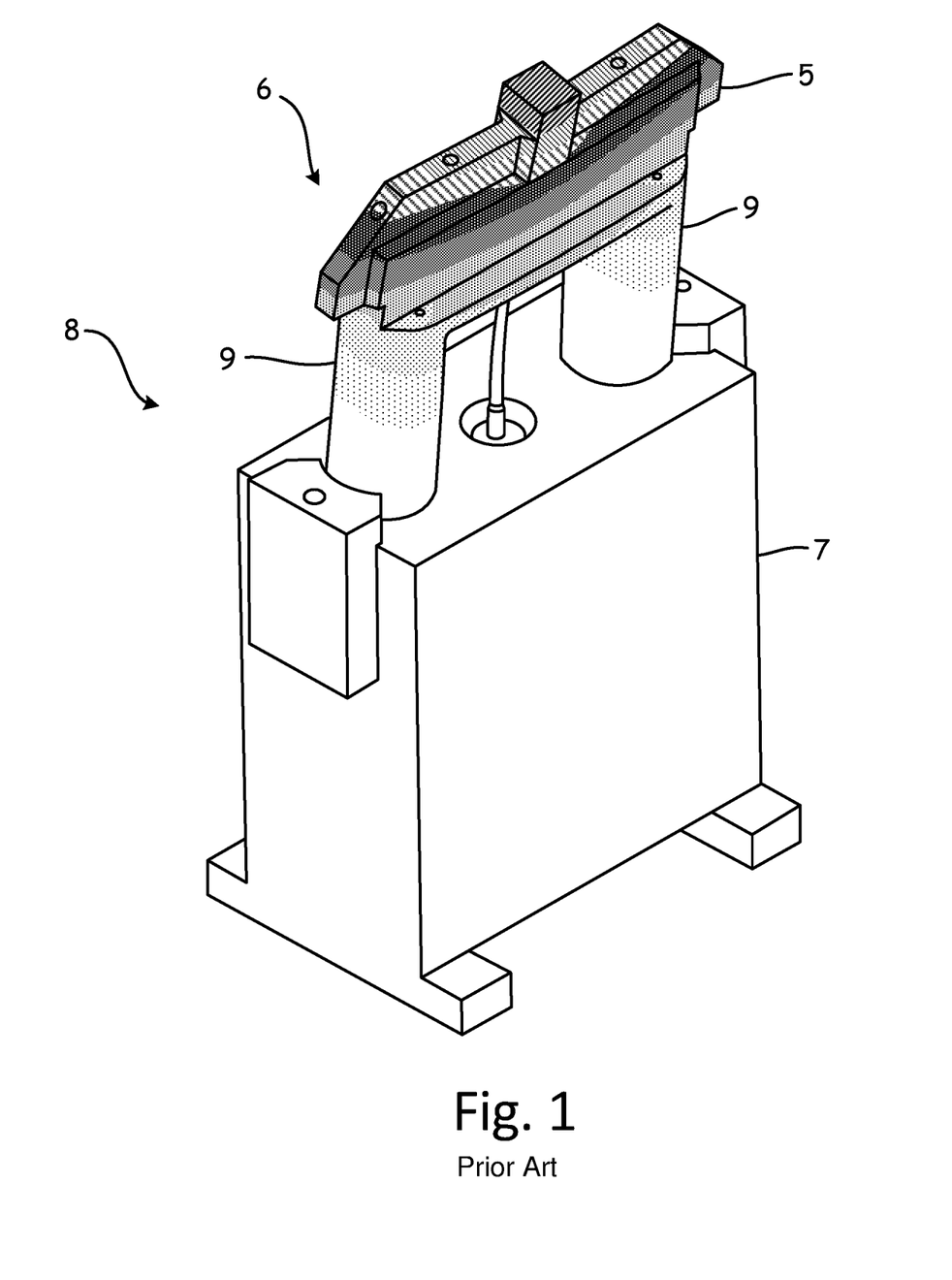
FIG. 1 is a schematic illustration of a mode of mechanical vibration resonance in a testing system for applying force or displacement to a test specimen.

Servo-hydraulic actuated testing systems are often used to dynamically test elastomer materials and components. Servo-hydraulic actuation provides a high power prime mover which accommodates high velocity and high force input motion. A requirement for many elastomer tests is a high frequency motion excitation. These frequencies can be as high as 1000 Hz or more which is needed to study the response of the material or component used for isolating mechanical vibrations. Testing at these high frequencies creates a very difficult design requirement on the mechanical structure of the testing frame. FIG. 1 is a schematic representation of mechanical vibration resonance where the vibration resonance is illustrated by a crosshead 5 at the top of a testing machine 6 that appears to be leaning with respect to a base 7. The top of the crosshead 5 vibrates the most with the portions below the top experiencing vibration but at a lesser degree as represented by the various patterns thereon. However, it is important to note this is one type of modeled vibration resonance and should not considered limiting. For instance, the base 7 of the testing machine 6 can also experience vibration resonance. In most cases, mechanical resonant modes in a testing frame 8 (base 7, cross-head 5, support columns 9, etc.) define the maximum allowable frequency for a particular testing frame 8 since the resonant modes disrupt the measurements.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the invention is a testing system for applying loads to a test specimen. The testing system includes an actuator and a first support portion supporting the actuator. The actuator is configured to support a first end of the test specimen, while a second support portion configured to support a second end of the test specimen. In various embodiments, combination of sensors that can include displacement sensor and/or accelerometer(s) provide associated output signals that are received by a displacement compensator that is configured to provide a displacement output signal indicative of differential displacement between first end and the second end of the test specimen. The new displacement measurement technique minimizes the effect of at least some frame mechanical resonances in testing of a test specimen such as the frame mechanical resonances at least at higher frequencies.

In a first embodiment, a testing system for applying loads to a test specimen includes an actuator, a first support portion supporting the actuator, the actuator configured to support a first end of the test specimen, and a second support portion configured to support a second end of the test specimen. A first sensor is configured to provide a first output signal indicative of displacement of the first end of the test specimen. An acceleration sensor is configured to measure acceleration of a component of the system and provide a second output signal. A displacement compensator is configured to receive the first output signal and the second output signal provide a displacement output signal indicative of differential displacement between first end and the second end of the test specimen. The first sensor can comprise a displacement sensor configured to measure displacement of the first end of the test specimen, which can be directly or indirectly for example through measuring displacement of a piston rod of the actuator, the piston rod supporting the first end of the specimen. Other measurement of other fixture elements connected to the first end of the specimen and not to the second end such as a grip to hold the first specimen end can be also be used.

In one embodiment, the acceleration sensing device is operably coupled to the first support portion; however, other frame elements of the test system that undergo acceleration. It may be beneficial to use one or a combination of other frame components that undergo similar acceleration as that of the first end of the test specimen.

In another embodiment, the test system includes a second acceleration sensor configured to provide a third output signal indicative of acceleration of the second end of the test specimen, wherein the displacement compensator is configured to receive the first output signal, the second output signal and the third output signal and provide the displacement output signal indicative of differential displacement between first end and the second end of the test specimen.

In yet another embodiment, the first sensor comprises a first accelerometer configured to measure acceleration of the first end of the test specimen, the first output signal comprising a first accelerometer output signal, and wherein the acceleration sensing device is a second accelerometer configured to measure acceleration of the second end of the test specimen, the second output signal comprising a second accelerometer output signal. The displacement compensator is configured to obtain a difference acceleration signal indicative of a difference between the first and second acceleration output signals, the displacement compensator further comprising a double integrator configured to obtain a double integration of the difference acceleration signal to provide the displacement output signal.

In yet a further embodiment, the first sensor comprises a first accelerometer configured to measure acceleration of the first end of the test specimen, the first output signal comprising a first accelerometer output signal, and wherein the acceleration sensing device is a second accelerometer configured to measure acceleration of the second end of the test specimen, the second output signal comprising a second accelerometer output signal. The displacement compensator is configured to obtain a first displacement signal being a double integration of the first acceleration output signal and a second displacement output signal being a double integration of the second acceleration output signal, the corrector further configured to obtain a difference of the first displacement signal and the second displacement signal to provide the displacement output signal.

If desired, the first accelerometer is mounted to a piston rod of the actuator. However, other locations include other fixture elements connected to the first end of the specimen and not to the second end such as a grip to hold the first specimen end can be also be used. If further desired, the acceleration sensing device is a second accelerometer configured to measure acceleration of the second end of the test specimen, the second output signal comprising a second accelerometer output signal, and the testing system further comprising a first specimen grip fixedly mounted to the actuator and configured to support the first end of the test specimen and a second specimen grip fixedly mounted to the second support portion and configured to support the second end of the test specimen. The second accelerometer can be mounted to the second specimen grip or other fixturing directly connected to the second end of the test specimen and not the first end of the test specimen. Another example of such fixturing includes the second accelerometer being mounted to a component of the force transducer coupled to the second end of the test specimen.

In another embodiment, a testing system for applying loads to a test specimen includes a first specimen grip for the test specimen, a second specimen grip for a test specimen, a force transducer configured to support the second specimen grip, a base configured to support the force transducer and an actuator supported by the base, the actuator configured to support the first specimen grip. A first accelerometer is configured to measure acceleration of a first end of the test specimen when mounted in the first specimen grip and provide a first acceleration output signal. A second accelerometer is configured to measure acceleration of a second end of the test specimen when mounted in the second specimen grip and provide a second acceleration output signal. A displacement compensator is configured to receive the first and second acceleration output signals and provide a displacement output signal indicative of differential displacement between first end and the second end of the test specimen.

In a further embodiment, the second accelerometer is mounted to a component of the force transducer or other fixturing directly connected to the second end of the test specimen. Likewise, if desired, the first accelerometer can be mounted to a piston rod of the actuator or other fixturing directly connected to the first end of the test specimen.

In one embodiment, the displacement compensator can be configured to obtain a difference acceleration signal indicative of a difference between the second and first acceleration output signals, the displacement compensator further comprising a double integrator configured to obtain a double integration of the difference acceleration signal to provide the displacement output signal. In another embodiment, the displacement compensator is configured to obtain a second displacement signal being a double integration of the second acceleration output signal and a first displacement output signal being a double integration of the first acceleration output signal, the corrector further configured to obtain a difference of the second displacement signal and the first displacement signal to provide the displacement output signal.

A method of providing displacement correction in a testing machine having an actuator applying force or displacement to a test specimen is also disclosed. The method includes applying a force to a first end of the test specimen; supporting a second end of the test specimen in at least a substantially fixed position; obtaining a signal indicative of displacement of the first end of the test specimen; measuring acceleration of a component of the testing machine; and obtaining an output signal indicative of differential displacement between second end and the first end of the test specimen using the signal indicative of displacement of the first end of the test specimen and the measured acceleration of the second end of the test specimen.

In a further embodiment, a displacement sensor provides the signal indicative of displacement of the first end of the test specimen, which can be from any fixturing connected directly thereto such as a piston rod of the actuator, the piston rod supporting the first end of the specimen, and/or and the component comprises the first support portion.

Obtaining the signal indicative of displacement of the first end of the test specimen can comprise measuring acceleration of the first end of the test specimen, and measuring acceleration of a component of the testing machine comprises measuring acceleration of a component coupled to the second end of the test specimen under test, and wherein obtaining the output signal cam comprise obtaining a difference acceleration signal indicative of a difference between the first and second acceleration signals and double integrating the difference acceleration signal.

In another embodiment, obtaining the output signal can comprise obtaining a second displacement signal being a double integration of the second acceleration signal and a first displacement signal being a double integration of the first acceleration signal and obtaining difference of the second displacement signal and the first displacement signal.

Measuring acceleration of the second end of the test specimen can comprise using a second accelerometer mounted to a force transducer supporting the second end of the test specimen. Likewise, measuring acceleration of the first end of the test specimen can comprise using a first accelerometer mounted to a specimen grip used to support the first end of the test specimen or mounted to a piston rod of an actuator applying the force to the first end of the test specimen.

DESCRIPTION OF EXEMPLARY EMBODIMENTS

Figure 2:
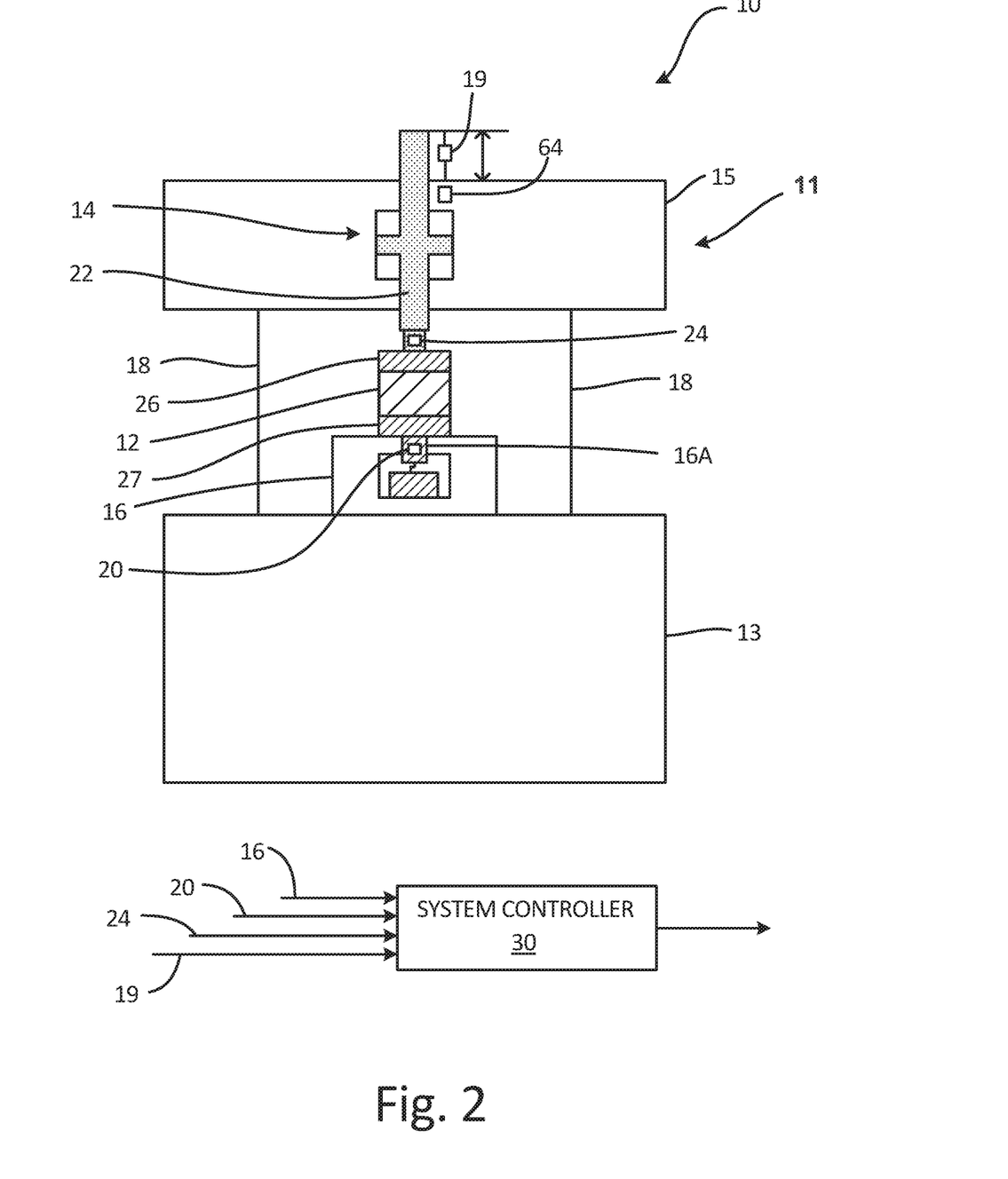
FIG. 2 is a schematic illustration of a testing system having aspects of the disclosure.

The purpose of a typical testing system 10 schematically illustrated in FIG. 2 (particularly is to measure forces transmitted through a specimen 12 (material or component) for a particular displacement excitation input from an actuator 14. Generally, the testing system 10 comprises a test frame 11 having a second support portion such as a base 13 and a first support portion 15. In the embodiment illustrated, the first support portion 15 comprises a cross-head supported by columns 18; however it should be understood the illustrated embodiment is merely exemplary. In addition, in this embodiment, the actuator 14 is mounted in the cross-head 15; however, in other embodiments, the actuator 14 can be mounted in the base 13.

Sometimes testing can be difficult typically at high frequencies (greater than 100 Hz). At such frequencies, the vibrations in the surrounding mechanical structures can produce errors in force measurements from a force transducer or load cell 16 and/or displacement transducer measurements from a displacement transducer 19. A common technique to improve the force measurement in the presence of these vibrations is a technique called acceleration compensation such as described in U.S. Pat. No. 7,331,209 and published U.S. patent application US20130305840 A1, both of which are incorporated herein in their entirety. Briefly, with reference to FIG. 2, at higher frequencies (for instance greater than 100 Hz), when the force transducer 16 experiences a vibrational acceleration, there is an error in its output which is proportional to the mass of any fixturing attached to an active side 16A (portion that moves due to the force applied, schematically illustrated in FIG. 2) of the force transducer 16 and the acceleration of the force transducer 16. A technique used to compensate for this inertial error is to add a compensation factor equal to the measured acceleration of the force transducer 16, times the estimated mass of the fixturing to the measured force. Most often an accelerometer 20 is located directly on the active side 16A of the force transducer 16.

Referring further to FIG. 2, for measuring displacement, the displacement transducer 19 is attached to an actuator piston rod 22 of the actuator 14. For example, the displacement transducer 19 can be a linear variable displacement transducer (LVDT), although other forms of displacement sensors using optical, capacitive, magnetostrictive elements can also be used. For measuring displacement at high frequencies, an accelerometer 24 is attached to a moving portion of the specimen 12 such as to the actuator piston rod 22 although other locations such as being located in a first test specimen grip, schematically illustrated at 26, can be used. (A second test specimen grip 27 is used to support an end of the test specimen 12 opposite the first test specimen grip 26). The acceleration output signal from the accelerometer 24 is received by a system controller 30. The acceleration output signal from the accelerometer 24 is processed (e.g. numerically double integrated) to obtain a displacement measurement of the motion excitation input from the actuator piston rod 22. It should be noted that this acceleration derived motion input measurement (herein by way of example at the actuator piston rod 22) is relative to inertial ground since the accelerometer 24 is used.

As mentioned above, vibrations can often be present on the force transducer 16. In addition to causing errors in the force measurement, this vibration results in errors in the "relative" displacement imposed on the specimen 12. The "relative" displacement is the deflection across the specimen 12, or said another way, the displacement of the upper portion of the test specimen 12 (herein measured by way of example at the actuator piston rod 22) minus the displacement of a lower portion of the test specimen 12, which is connected to the base 13. It should be noted while characterizing the force generated by a specimen when a displacement motion is imposed on it, the more accurate displacement that determines the specimen force response is the relative displacement imposed on the specimen 12.

An aspect of the invention is a testing system for applying loads to a test specimen. The testing system includes the actuator 14 and the first support portion 15 supporting the actuator 14. The actuator 14 is configured to support a first end of the test specimen, while the second support portion 13 configured to support a second end of the test specimen. In various embodiments, combination of sensors that can include displacement sensor and/or accelerometer(s) provide associated output signals that are received by a displacement compensator such as 50, 50' or 60 illustrated in FIGS. 3A, 3B and 3C, respectively. Each displacement compensator is configured to provide a displacement output signal indicative of differential displacement between first end and the second end of the test specimen.

In a first embodiment a correction is made to the upper (herein piston actuator rod 22 mounted) accelerometer 24 to account for the deflection or motion on the assumed "fixed" side of the specimen 12. The fixed side of the specimen 12 in most cases is the side of the specimen 12 in which the force transducer 16 is attached, typically on a side opposite of the piston actuator rod 22. The term "fixed side" as used herein is a side or end of the test specimen 12 that is not directly connected to the piston actuator rod 22. As explained below, there is actual movement of the fixed side of the test specimen 12; however prior to this disclosure it was considered motionless or considered negligible.

Figure 3A:
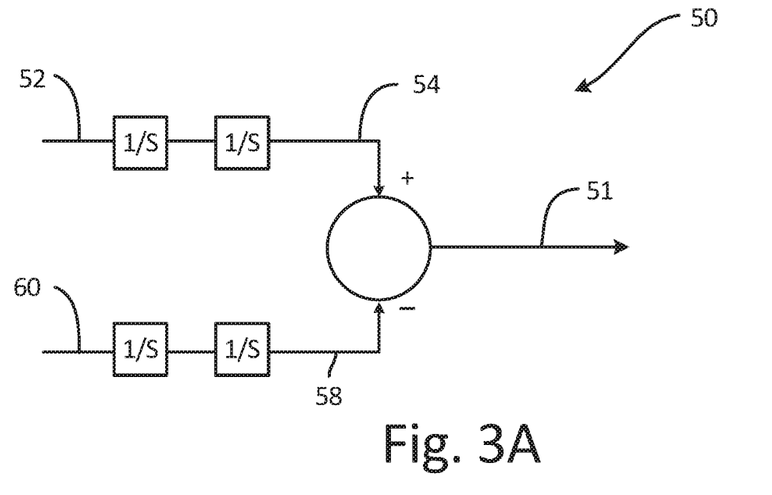
FIGS. 3A, 3B and 3C are block diagrams for processing signals from accelerometers.

A first displacement compensator or corrector 50 (FIG. 3A), which can be embodied in system controller 30, herein described measures vibration displacement of the second or fixed side of the test specimen 12, and subtracts this measured deflection from the piston actuator rod 22 measured displacement, which is indicative of displacement of a first side of the test specimen 12. Referring to FIG. 3A, the relative resultant displacement output signal 51 can be determined by taking a signal 52 indicative of displacement of the first side of the test specimen 12, for example as measured via piston actuator rod 22 (e.g. as ascertained by double integration of the piston rod accelerometer 24 to provide signal 54) and subtracting a signal 58 indicative of displacement of the second or fixed side of the test specimen 12 (e.g. double integration of a signal 60 from the accelerometer 20 on a base side of the test specimen 12). A first version of a displacement compensator or corrector is illustrated at 50 in FIG. 3A. However, since the integration process is a linear operation, the equivalent signal can be formulated by first subtracting the signals from the accelerometers 20 and 24 and then performing the double integration on the resulting signal to derive the differential displacement as illustrated in a displacement compensator or corrector 50' of FIG. 3B. In other words, either technique can be employed.

Figure 3B:
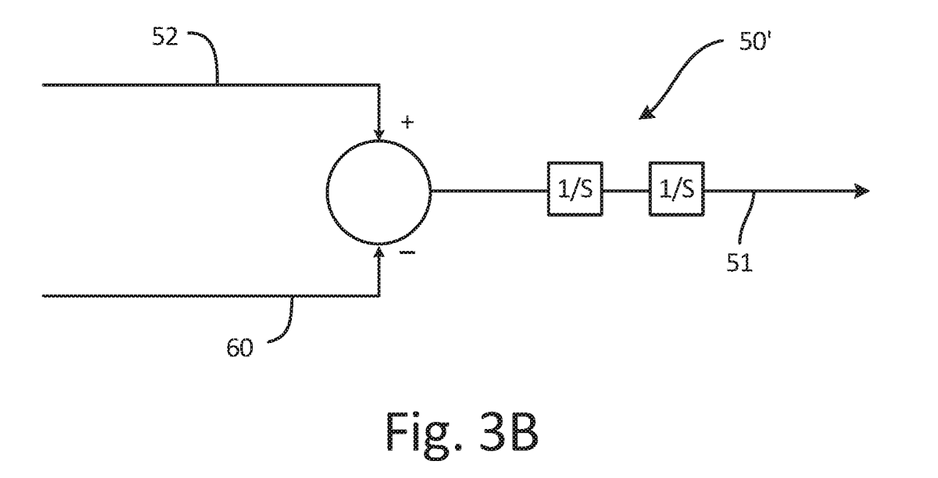
Figure 3C:
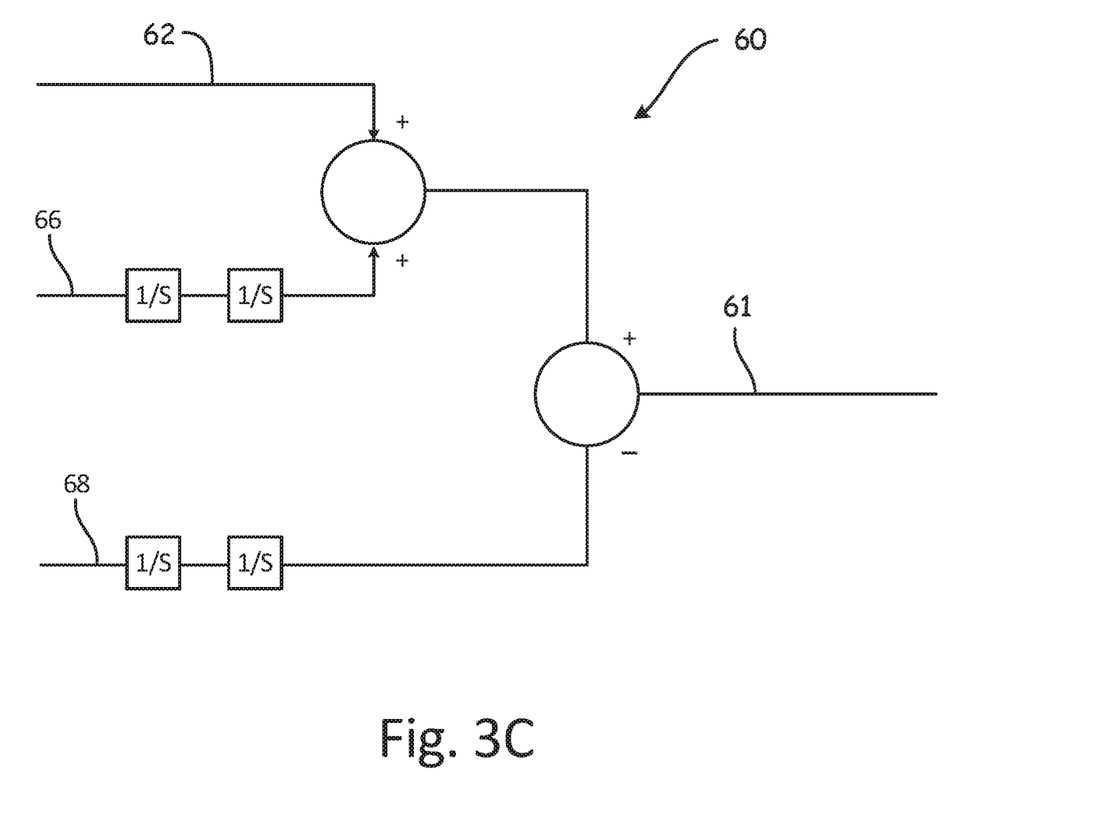

FIG. 3C illustrates another form of a displacement compensator 60. In this embodiment, an output displacement signal 62 is obtained from the displacement sensor 19. However, instead of using the acceleration measurement of the piston actuator rod 22 (or other accelerometers that move with the first end of the test specimen 12 such as on grip 26), an accelerometer 64 is provided on the first support portion or crosshead 15 so as to provide an output signal 66 indicative of acceleration of the crosshead 15. In one embodiment, location of the accelerometer 64 is proximate the mounting location of the displacement sensor 19 to the crosshead 15. In a first embodiment of the displacement compensator 60, the output signal from the accelerometer 20 is also used. In particular, a relative resultant displacement output signal 61 is obtained by adding the output displacement signal 62 from the displacement sensor 19 to the double integration of acceleration output signal 66 and then subtracting the double integration of the output signal 68 from accelerometer 20. This embodiment is particularly advantageous because there is no moving accelerometer on the first side of the test specimen 12 such as on the piston actuator rod 22. For instance, some test systems have very long piston motion that makes it very difficult or impractical to locate an accelerometer on the piston actuator rod 22. If the accelerometer 24 is mounted to the first end of the test specimen 12, or an element that moves therewith, an accelerometer cable connected to the accelerometer 24 may whip during fast motions causing connector strain or measurement error.

It should be noted that if an accelerometer on the second side of the test specimen 12 (accelerometer 20) is not present, or motion of the second side of the test specimen 12 is considered insignificant, the relative resultant displacement output signal 61 can be based on only adding the output displacement signal 62 from the displacement sensor 19 to the double integration of acceleration output signal 66. Even without the correction attributable to motion of the second end of the test specimen via accelerometer 20, this approach may still be appealing to eliminate the cable whip for large stroke actuators.

In U.S. Pat. No. 7,331,209 and published US patent application US20130305840 A1, the acceleration compensation accelerometer is located on the active side of the force transducer and is used to provide forms of acceleration compensation. If a testing system has the accelerometer already present on the active side 16A of the force transducer 16, the signal therefrom can also be used as discussed above to provide displacement compensation. Hence, an additional accelerometer to sense the second or base side of the test specimen 12 is not needed. This saves costs and labor because packaging of an additional base side accelerometer can be difficult due to size constraints. Hence, a simple implementation of providing displacement compensation for the test specimen 12 is to use the existing acceleration compensation acceleration signal on the active side 16A of the force transducer 12 as the base side acceleration measurement. However, it should be noted that if desired, an accelerometer mounted on the base side of the test specimen 12, or the specimen grip 27, or other elements connected thereto to provide a signal indicative of the base side of the test specimen 12.

The displacement compensators or correctors 50, 50' and 60 of FIGS. 3A, 3B and 3C may be embodied in hardware (analog and/or digital circuitry) and/or in software operable on a suitable computing device, such a digital signal processor, which also is circuitry. If implemented using digital circuitry, analog to digital converters as known in the art can first be used to digitize the signals from the accelerometers 20 and 24. The processing circuitry can further include without limitation logic arrays and a system on a chip implementation that integrates some if not all circuitry and components of a computer or other electronic system that processes digital signals, analog signals, and/or mixed digital and analog signals on a single chip substrate. The displacement compensator or corrector 50, 50', 60 may operate in a control loop in real-time where a resulting output displacement signal 51, 61 may be used to control operation of the actuator 14, which can be of any form such as but not limited to a hydraulic, pneumatic and/or electric actuator.

Compensation for displacement of the test specimen is particularly helpful when testing involves oscillating applied forces or displacements greater than 100 Hz applied to the test specimen. It is even more helpful as the required oscillations for testing increases and is in the range 500 Hz and/or greater than 1500 Hz.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. A testing system for applying loads to a test specimen, the testing system comprising:
   an actuator;
   a test frame having a first support portion and a second support portion coupled by columns, the first support portion supporting the actuator, the actuator configured to support a first end of the test specimen, and the second support portion configured to support a second end of the test specimen;
   a first sensor configured to provide a first output signal indicative of displacement of the first end of the test specimen;
   an acceleration sensor configured to measure acceleration of the first support portion or the second end of the test specimen and provide a second output signal indicative of the measured acceleration; and
   a displacement compensator configured to receive the first output signal and the second output signal and provide a displacement output signal indicative of differential displacement between the first end and the second end of the test specimen.

2. The testing system of claim 1 wherein the first sensor comprises a displacement sensor.

3. The testing system of claim 2 wherein the displacement sensor is configured to measure displacement of a piston rod of the actuator, the piston rod supporting the first end of the test specimen.

4. The testing system of claim 3 wherein the acceleration sensor is operably coupled to the first support portion.

5. The testing system of claim 4 and a second acceleration sensor configured to provide a third output signal indicative of acceleration of the second end of the test specimen, wherein the displacement compensator is configured to receive the first output signal, the second output signal and the third output signal and provide the displacement output signal indicative of differential displacement between first end and the second end of the test specimen.

6. The testing system of claim 1 wherein the first sensor comprises a first accelerometer configured to measure acceleration of the first end of the test specimen, the first output signal comprising a first accelerometer output signal, wherein the acceleration sensor is a second accelerometer configured to measure acceleration of the second end of the test specimen, the second output signal comprising a second accelerometer output signal, and wherein the displacement compensator is configured to obtain a difference acceleration signal indicative of a difference between the first and second acceleration output signals, the displacement compensator further comprising a double integrator configured to obtain a double integration of the difference acceleration signal to provide the displacement output signal.

7. The testing system of claim 1 wherein the first sensor comprises a first accelerometer configured to measure acceleration of the first end of the test specimen, the first output signal comprising a first accelerometer output signal, wherein the acceleration sensor is a second accelerometer configured to measure acceleration of the second end of the test specimen, the second output signal comprising a second accelerometer output signal, and wherein the displacement compensator is configured to obtain a first displacement signal being a double integration of the first acceleration output signal and a second displacement signal being a double integration of the second acceleration output signal, the displacement compensator further configured to obtain a difference of the first displacement signal and the second displacement signal to provide the displacement output signal.

8. The testing system of claim 1 wherein the first sensor comprises a first accelerometer configured to measure acceleration of the first end of the test specimen, the first output signal comprising a first accelerometer output signal, wherein the acceleration sensor is a second accelerometer configured to measure acceleration of the second end of the test specimen, the second output signal comprising a second accelerometer output signal, and wherein the first accelerometer is mounted to a piston rod of the actuator.

9. The testing system of claim 1 wherein the first sensor comprises a first accelerometer configured to measure acceleration of the first end of the test specimen, the first output signal comprising a first accelerometer output signal, wherein the acceleration sensor is a second accelerometer configured to measure acceleration of the second end of the test specimen, the second output signal comprising a second accelerometer output signal, and the testing system further comprising a first specimen grip fixedly mounted to the actuator and configured to support the first end of the test specimen and a second specimen grip fixedly mounted to the second support portion and configured to support the second end of the test specimen.

10. The testing system of claim 9 wherein the first accelerometer is mounted to the first specimen grip.

11. The testing system of claim 9 wherein the second accelerometer is mounted to the second specimen grip.

12. The testing system of claim 1 wherein the first sensor comprises a first accelerometer configured to measure acceleration of the first end of the test specimen, the first output signal comprising a first accelerometer output signal, wherein the acceleration sensor is a second accelerometer configured to measure acceleration of the second end of the test specimen, the second output signal comprising a second accelerometer output signal and further comprising a force transducer supporting the second end of the test specimen on the second support portion.

13. The testing system of claim 12 wherein the second accelerometer is mounted to the force transducer.

14. The testing system of claim 13 wherein the first accelerometer is mounted to a piston rod of the actuator.

15. A testing system for applying loads to a test specimen, the testing system comprising:
   a first specimen grip configured to engage a first end of the test specimen;
   a second specimen grip configured to engage a second end of the test specimen;
   a force transducer configured to support the second specimen grip;
   a base configured to support the force transducer;
   an actuator supported by the base, the actuator configured to support the first specimen grip;
   a first accelerometer configured to measure acceleration of a first end of the test specimen when mounted in the first specimen grip and provide a first acceleration output signal;
   a second accelerometer configured to measure acceleration of a second end of the test specimen when mounted in the second specimen grip and provide a second acceleration output signal; and
   a displacement compensator configured to receive the first and second acceleration output signals and provide a displacement output signal indicative of differential displacement between the first end and the second end of the test specimen.

16. The testing system of claim 15 wherein the second accelerometer is mounted to a component of the force transducer.

17. The testing system of claim 16 wherein the first accelerometer is mounted to a piston rod of the actuator.

18. The testing system of claim 16 wherein the first accelerometer is mounted to the first specimen grip.

19. The testing system of claim 15 wherein the displacement compensator is configured to obtain a difference acceleration signal indicative of a difference between the second and first acceleration output signals, the displacement compensator further comprising a double integrator configured to obtain a double integration of the difference acceleration signal to provide the displacement output signal.

20. The testing system of claim 15 wherein the displacement compensator is configured to obtain a second displacement signal being a double integration of the second acceleration output signal and a first displacement signal being a double integration of the first acceleration output signal, the displacement compensator further configured to obtain a difference of the second displacement signal and the first displacement signal to provide the displacement output signal.

21. A method of providing displacement correction in a testing machine having an actuator applying force or displacement to a test specimen, the method comprising:
   supporting a second end of the test specimen in at least a substantially fixed position;
   applying a force to a first end of the test specimen;
   measuring acceleration of the second end of the test specimen under test;
   measuring acceleration or displacement of the first end of the test specimen; and
   obtaining an output signal indicative of differential displacement between the second end and the first end of the test specimen using the measured acceleration of the second end of the test specimen and the measured acceleration or displacement of the first end of the test specimen.

22. The method of claim 21 wherein a displacement sensor measures displacement of the first end of the test specimen.

23. The method of claim 22 wherein the displacement sensor measures displacement of a piston rod of the actuator, the piston rod supporting the first end of the test specimen.

24. The method of claim 21 and wherein obtaining the output signal comprises obtaining a difference acceleration signal indicative of a difference between the measured accelerations of the first and second ends of the test specimen and double integrating the difference acceleration signal.

25. The method of claim 21 wherein obtaining the output signal comprises obtaining a second displacement signal being a double integration of the measured acceleration of the second end and a first displacement signal being a double integration of the measured acceleration of the first end and obtaining difference of the second displacement signal and the first displacement signal.

26. The method of claim 21 wherein measuring acceleration of the second end of the test specimen comprises using a second accelerometer mounted to a force transducer supporting the second end of the test specimen.

27. The method of claim 26 wherein measuring acceleration of the first end of the test specimen comprises using a first accelerometer mounted to a specimen grip used to support the first end of the test specimen or mounted to a piston rod of an actuator applying the force to the first end of the test specimen.

* * * * *